(12) United States Patent
Chardès et al.

(10) Patent No.: US 11,001,634 B2
(45) Date of Patent: *May 11, 2021

(54) ANTI-HUMAN-HER3 ANTIBODIES AND USES THEREOF

(71) Applicants: GAMAMABS PHARMA, Toulouse (FR); INSTITUT NATIONAL DE LA SANTÉ ET DE LA RECHERCHE MÉDICALE (INSERM), Paris (FR); UNIVERSITE DE MONTPELLIER, Montpellier (FR); INSTITUT REGIONAL DU CANCER DE MONTPELLIER, Montpellier (FR)

(72) Inventors: Thierry Chardès, Assas (FR); Olivier Dubreuil, Mauressac (FR); André Pelegrin, Montpellier (FR); Christel Larbouret, Valflaunès (FR); Jean-François Prost, Versailles (FR); Jean-Marc Barret, Castres (FR); Stéphane Degove, Pantin (FR)

(73) Assignees: GAMAMABS PHARMA, Toulouse (FR); INSTITUT NATIONAL DE LA SANTÉ ET DE LA RECHERCHE MÉDICALE (INSERM), Paris (FR); UNIVERSITE DE MONTPELLIER, Montpellier (FR); INSTITUT REGIONAL DU CANCER DE MONTPELLIER, Montpellier (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/571,720

(22) PCT Filed: May 2, 2016

(86) PCT No.: PCT/EP2016/059739
§ 371 (c)(1),
(2) Date: Nov. 3, 2017

(87) PCT Pub. No.: WO2016/177664
PCT Pub. Date: Nov. 10, 2016

(65) Prior Publication Data
US 2018/0155433 A1    Jun. 7, 2018

(30) Foreign Application Priority Data

May 6, 2015   (EP) ..................................... 15305695

(51) Int. Cl.
| | | |
|---|---|---|
| *C07K 16/28* | (2006.01) | |
| *C07K 16/32* | (2006.01) | |
| *A61K 39/395* | (2006.01) | |
| *A61P 35/00* | (2006.01) | |
| *A61K 39/00* | (2006.01) | |

(52) U.S. Cl.
CPC .......... *C07K 16/2863* (2013.01); *A61P 35/00* (2018.01); *C07K 16/32* (2013.01); *A61K 2039/505* (2013.01); *C07K 2317/24* (2013.01); *C07K 2317/41* (2013.01); *C07K 2317/73* (2013.01); *C07K 2317/92* (2013.01)

(58) Field of Classification Search
CPC combination set(s) only.
See application file for complete search history.

(56) References Cited

FOREIGN PATENT DOCUMENTS

WO    WO 2012/156532    * 11/2012

OTHER PUBLICATIONS

Lazrek et al (Neoplasia, 2013, 15:335-347).*
Mod et al (Cytotechnology, 2007, 55:109-114).*

* cited by examiner

*Primary Examiner* — Laura B Goddard
(74) *Attorney, Agent, or Firm* — W&C IP

(57) ABSTRACT

The present disclosure relates to a neuregulin non competitive allosteric anti-human-HER3 antibody having a human constant region; and less than 65% of the glycan structures carried by the glycosylation site of the antibody comprises a fucose molecule. The antibody is characterized by its variable sequences.

21 Claims, 6 Drawing Sheets

Specification includes a Sequence Listing.

ANTI-HUMAN-HER3 ANTIBODIES AND USES THEREOF

FIELD OF THE INVENTION

The present invention relates to chimeric low-fucose neuregulin (NRG)-non competitive allosteric anti-human-HER3 antibodies and uses thereof in therapeutic methods.

BACKGROUND OF THE INVENTION

The human epidermal growth factor receptor ErbB/HER family of receptor tyrosine kinases (RTK) includes four members: EGFR (ErbB1/HER1), HER2 (c-Neu, HER2), HER3 (ErbB3/HER3) and HER4 (ErbB4/HER4). The HER receptors comprise an extracellular glycosylated domain consisting of four structural domains, marked 1 to 4, followed by a transmembrane domain and an intracellular C-terminal part containing a kinase domain for coupling to signalling pathways. Except for HER3, the intracellular region contains a tyrosine kinase activity. Signalling is mediated through ligand-induced receptor dimerization and subsequent phosphorylation that leads to the activation of cytoplasmic signalling pathways. HER2 has no specific ligand because it is naturally under an "active" conformation. The other HER receptors exist as inactive monomers with the molecules folded in such a way to prevent dimerization. Ligand binding to domains 1 and 3 induces major conformational changes ultimately exposing the dimerization loop in domain 2 of the receptor. This exposure of the dimerization loop allows for receptor dimerization.

The HER3 receptor, that has been first described in 1990, is the only HER family member receptor that shows low kinase activity and downstream signalling is achieved through heterodimerization. Thus, the HER3 receptor, as a monomer, is called "non-self" and cannot form homodimers. Binding of the ligand neuregulin (NRG) to HER3 receptor triggers the heterodimerization of HER3 with the others HER family receptors (HER2 preferentially). Within the heterodimer, the HER3 kinase domain acts as an allosteric activator of its HER family partner.

HER3 is implicated in tumorigenesis of various cancers including breast and ovarian cancer (Lee-Hoeflich S T, Cancer Res. 2008; McIntyre E, Breast Cancer Res Treat. 2010; Tanner B, J Clin Oncol. 2006). HER3 expression correlates with tumor progression and reduced patient survival in malignant melanoma and metastases, and is associated with decrease survival in ovary cancer. Importantly, in breast cancer, tumors with low HER2 expression, which are not eligible to Herceptin treatment, often are "programmed" to strongly express HER3 (Smith et al. Br. J. Cancer 2004), and HER2+++ tumors, which become resistant to Herceptin after prolonged treatment, are "re-programmed" to strongly express HER3 (Narayan, Cancer Res. 2009). Cetuximab resistance was also associated with HER3 over-expression in lung cancer (Wheeler, Oncogene 2008) and colorectal carcinomas (Lu Cancer Res 2007), together with dysregulation of EGFR internalization/degradation. Recently, HER3 over-expression was significantly associated with worse metastasis-free survival in colorectal carcinoma (Ho-Pun-Cheung, Int J Cancer 2010). Thus, HER3 over-expression and compensatory signalling through activation of the PI3K/AKT pathway are implicated in the development of resistance to treatment with HER-targeted therapies (antibodies and TKI) (Wheeler 2008, Lu 2007, Narayan, 2009, Sergina, 2007) but also to treatment with IGFR-targeted therapies (Desbois-Mouthon, Clin Cancer Res 2009) and with chemotherapeutic agents (Kruser, Exp Cell Res 2010).

All these findings suggest that HER3-targeted agents, and in particular antibodies, might help to further understand the role of HER3 signalling in cancers and especially be used as efficient immunotherapeutics.

Many therapeutic antibodies, already commercialized or not, have been developed against HER3 in therapeutic oncology.

For example, two human antibodies are proposed by Merrimack Pharmaceuticals/Sanofi Aventis (MM-121 antibody; PCT WO2008/100624) and U3 PharmaAG/Daiichi Sankyo/Amgen (U3-1287 or AMG-888; PCT WO2007/077028). One HER2/HER3 bispecific antibody MM-111 (Merrimack Pharmaceuticals; PCT WO2005/117973, WO2006/091209) is involved in phase I/II clinical trials, alone or in combination with trastuzumab or lapatinib, in HER2-amplified breast cancer.

All these antibodies block the heregulin-binding site of the HER3 receptor, thus reducing these antibody therapies to ligand-addicted tumors.

However, in order to bypass the resistance to targeted therapies or chemotherapies in resistant HER2-amplified breast cancer and to broaden the application field of targeted therapies to HER2 low breast cancer, which are currently not eligible for such treatment, or to treat triple-negative breast cancers, which express HER3 and for which no targeted therapy is available yet, the targeting of HER3 with antibodies that are not directed to the heregulin-binding site of HER3 was explored.

A variety of NRG-competitive and NRG-non competitive anti-human HER3 antibodies were disclosed in the art (Lazrek et al., Neoplasia March 2013; Vol. 15; N °3, pp. 335-347). Lazrek et al. (2013) disclosed assays involving various anti-HER3 antibodies of unknown structures which were termed H3A-122, H4B-25, H4B-121, 9F7-F11, 11G10-D2, 12H8-B11, 14H1-H8, 15D4-F2 and 16D3-C1, respectively. Illustratively, Lazrek et al. (2013) disclosed a murine anti-human HER3 antibody termed 9F7-F11, which antibody was shown to be NRG-non competitive.

Further, Lazrek et al. (2013) have shown the existence of an in vitro NRG-dependent increase of the 9F7-F11 binding to HER3.

The mechanisms by which NRG increases the binding of 9F7-F11 to its epitope have not yet been discovered. However, without being bound by the theory, it may be assumed that the binding of NRG to its receptor leads to a conformational change in the structure of HER3, leading either to a better availability of the epitope of 9F7-F11 and/or to a structural modification of the epitope that provides a better affinity with 9F7-F11.

However, despite an in vitro increase in the binding of 9F7-F11 to HER3 in the presence of its ligand neuregulin, 9F7-F11 did not exert increased in vivo anti-tumor activity against NRG-expressing tumor tissue, as compared with NRG-competitive antibodies (Lazrek et al., 2013).

The results of Lazrek et al. (2013) showed that an anti-tumor effect of the same degree was obtained with most of the antibodies that they have assayed, irrespective of the identity of the HER3 domain that they recognize, and thus also irrespective of whether these antibodies consist of NRG-non competitive anti-HER3 antibodies or in contrast consist of NRG-competitive anti-HER3 antibodies as it is the case e.g. for the 9F7-F11 antibody and the 16D3-C1 antibody, respectively. These authors concluded that all of these anti-HER3 antibodies appeared to all act through a single mechanism of action, namely an inhibition of the NRG-induced phosphorylation of HER3 which finally impaired HER2/HER3 heterodimer formation.

There remains a need in the art for availability of anti-HER3 antibodies aimed at treating HER3 positive cancers, including anti-HER3 antibodies having high anti-tumor activity against NRG-addicted tumors.

SUMMARY OF THE INVENTION

The present invention discloses an anti-human HER3 antibody comprising at least one of the CDRs selected from the group consisting of:
  a H-CDR1 having at least 90% or 95% identity with a sequence set forth as SEQ ID NO: 2;
  a H-CDR2 having at least 90% or 95% identity with a sequence set forth as SEQ ID NO: 3;
  a H-CDR3 having at least 90% or 95% identity with a sequence set forth as SEQ ID NO: 4;
  a L-CDR1 having at least 90% or 95% identity with a sequence set forth as SEQ ID NO: 6;
  a L-CDR2 having at least 90% or 95% identity with a the amino acid sequence SAS; and
  a L-CDR3 having at least 90% or 95% identity with a sequence set forth as SEQ ID NO: 8;
  said antibody having a human constant region; and
less than 65% of the glycan structures carried by the glycosylation site of the antibody comprise a fucose molecule.

In particular, the present invention discloses a neuregulin non competitive allosteric anti-human HER3 antibody comprising at least one of the CDRs selected from the group consisting of:
  a H-CDR1 having a sequence set forth as SEQ ID NO: 2;
  a H-CDR2 having a sequence set forth as SEQ ID NO: 3;
  a H-CDR3 having a sequence set forth as SEQ ID NO: 4;
  a L-CDR1 having a sequence set forth as SEQ ID NO: 6;
  a L-CDR2 having a the amino acid sequence SAS; and
  a L-CDR3 having a sequence set forth as SEQ ID NO: 8;
  said antibody having a human constant region; and
less than 65% of the glycan structures carried by the glycosylation site of the antibody comprise a fucose molecule.

The present invention also discloses a neuregulin non competitive allosteric anti-human HER3 antibody comprising:
  (a) a heavy chain wherein the variable domain comprises:
  a H-CDR1 having at least 90% or 95% identity with a sequence set forth as SEQ ID NO: 2;
  a H-CDR2 having at least 90% or 95% identity with a sequence set forth as SEQ ID NO: 3; and
  a H-CDR3 having at least 90% or 95% identity with a sequence set forth as SEQ ID NO: 4;
  and
  (b) a light chain wherein the variable domain comprises at least a CDR having a sequence chosen from the group consisting of:
  a sequence having at least 90% or 95% identity with a sequence set forth as SEQ ID NO: 6 as L-CDR1,
  a sequence having at least 90% or 95% identity with the amino acid sequence SAS as L-CDR2, and
  a sequence having at least 90% or 95% identity with a sequence set forth as SEQ ID NO: 8 as L-CDR3;
  said antibody having a human constant region; and
less than 65% of the glycan structures carried by the glycosylation site of the antibody comprise a fucose molecule.

A first object of the present invention is thus a neuregulin non competitive allosteric anti-human HER3 antibody comprising:
  (a) a heavy chain wherein the variable domain comprises:
  a H-CDR1 having a sequence set forth as SEQ ID NO: 2;
  a H-CDR2 having a sequence set forth as SEQ ID NO: 3; and
  a H-CDR3 having a sequence set forth as SEQ ID NO: 4; and
  (b) a light chain wherein the variable domain comprises at least a CDR selected from the group consisting of:
  a L-CDR1 having a sequence set forth as SEQ ID NO:6,
  a L-CDR2 having the amino acid sequence SAS; and
  a L-CDR3 having a sequence set forth as SEQ ID NO:8;
  said antibody having a human constant region; and
  less than 65% of the glycan structures carried by the glycosylation site of the antibody comprise a fucose molecule.

According to an embodiment, the antibody of the invention comprises a light chain variable region comprising a sequence having at least 90% or 95% identity with the sequence set forth as SEQ ID NO:6 as L-CDR1, a sequence having at least 90% or 95% identity with the amino acid sequence SAS as L-CDR2 and a sequence having at least 90% or 95% identity with the sequence set forth as SEQ ID NO:8 as L-CDR3.

In particular, the antibody of the invention comprises a light chain variable region comprising a L-CDR1 having a sequence set forth as SEQ ID NO:6, a L-CDR2 having the amino acid sequence SAS and a L-CDR3 having a sequence set forth as SEQ ID NO:8.

According to a further embodiment, the heavy chain variable region of the antibody of the invention has a sequence having at least 90% or 95% identity with the amino acid sequence set forth as SEQ ID NO: 1 and/or the light chain variable region has a sequence having at least 90% or 95% identity with the amino acid sequence set forth as SEQ ID NO: 5.

In particular, the heavy chain variable region of the antibody of the invention having a sequence having at least 90% or 95% identity with the amino acid sequence set forth as SEQ ID NO: 1 has:
  a H-CDR1 having a sequence set forth as SEQ ID NO: 2;
  a H-CDR2 having a sequence set forth as SEQ ID NO: 3; and
  a H-CDR3 having a sequence set forth as SEQ ID NO: 4.

In particular, the light chain variable region having a sequence having at least 90% or 95% identity with the amino acid sequence set forth as SEQ ID NO: 5 has:
  a L-CDR1 having a sequence set forth as SEQ ID NO:6,
  a L-CDR2 having a the amino acid sequence SAS; and
  a L-CDR3 having a sequence set forth as SEQ ID NO:8.

Preferably, the heavy chain variable region of said antibody has the amino acid sequence set forth as SEQ ID NO: 1 and/or the light chain variable region has the amino acid sequence set forth as SEQ ID NO: 5. More preferably, the heavy chain variable region of said antibody has the amino acid sequence set forth as SEQ ID NO: 1 and the light chain variable region has the amino acid sequence set forth as SEQ ID NO: 5.

According to another embodiment, the heavy chain of the antibody of the invention has the amino acid sequence having at least 90% or 95% identity with the amino acid sequence set forth as SEQ ID NO: 9 and/or the light chain of said antibody has the amino acid sequence having at least 90% or 95% identity with the amino acid sequence set forth as SEQ ID NO: 10.

Preferably, the heavy chain of said antibody has the amino acid sequence set forth as SEQ ID NO: 9 and/or the light chain of said antibody has the amino acid sequence set forth as SEQ ID NO: 10. More preferably, the heavy chain of said antibody has the amino acid sequence set forth as SEQ ID NO: 9 and the light chain of said antibody has the amino acid sequence set forth as SEQ ID NO: 10.

According to a further embodiment, an antibody according to the invention is such that less than 50% of the glycan structures carried by the glycosylation site of the antibody comprise a fucose molecule, preferably less than 40%, more preferably less than 30%, in particular less than 20%.

According to a particular embodiment, the antibody of the invention is a chimeric antibody, preferably a chimeric mouse/human antibody, and preferably a humanized antibody.

A second object of the invention relates to a nucleic acid sequence encoding at least for an heavy chain or light chain of a monoclonal antibody according to the invention, preferably for an antibody of the invention.

A third object of the invention relates to a vector comprising a nucleic acid according to the invention.

A forth object of the invention relates to a host cell comprising a nucleic acid according to the invention or a vector according to the invention.

A fifth object of the invention relates to a pharmaceutical composition comprising at least an antibody according to the invention and a pharmaceutically acceptable carrier.

A sixth object of the invention relates to an immunoconjugate comprising the antibody of the invention linked to a therapeutic agent.

A seventh object of the invention relates to a pharmaceutical composition comprising at least the immunoconjugate according to the invention and a pharmaceutically acceptable carrier.

An eighth object of the invention relates to the antibody and/or the immunoconjugate according to the invention, for its use as a drug.

A ninth object of the invention relates to the antibody and/or the immunoconjugate according to the invention for its use in the treatment of a cancer associated with the expression of HER3 wherein neuregulin is present, in particular neuregulin 1β, in a subject.

A tenth object of the invention relates to the antibody and/or the immunoconjugate according to the invention for its use in the inhibiting growth of tumor cells associated with the expression of HER3 wherein neuregulin is present, in particular neuregulin 1β, in a subject.

According to an embodiment, the neuregulin present is secreted by the tumor and/or by the tissues and/or organs surrounding the tumor. In a particular embodiment, the tumor is neuregulin-dependant, in particular neuregulin 1β-dependant.

In order to determine if NRG, and for example NRG1α or NRG1β, is present according to the invention, a well known method of immunohistochemistry can be applied as described in Gilmour et al. December 2002, Vol. 8, pp. 3933-3942.

According to another embodiment, neuregulin, and in particular neuregulin 1β, is present due to its administration to the subject before, after, or at the same time as the antibody and/or the immunoconjugate.

In a particular embodiment, the cancers or tumor cells associated with the expression of HER3 considered in the present invention are chosen among squamous cell cancer, small-cell lung cancer, non-small cell lung cancer, gastric cancer, pancreatic cancer, glial cell tumors, such as glioblastoma and neurofibromatosis, cervical cancer, ovarian cancer, liver cancer, bladder cancer, hepatoma, breast cancer, colon cancer, melanoma, colorectal cancer, endometrial carcinoma, salivary gland carcinoma, kidney cancer, renal cancer, prostate cancer, vulval cancer, thyroid cancer, hepatic carcinoma and head and neck cancers.

They are preferably chosen among breast cancer, ovarian cancer, small-cell lung cancer, non-small cell lung cancer, melanoma, pancreatic cancer and colorectal cancer, and more particularly among breast cancer, ovarian cancer and pancreatic cancer.

Abscissa: Nature of the antibody used. Ordinate: % of specific lysis of the targeted tumor cells.

Figure 5:
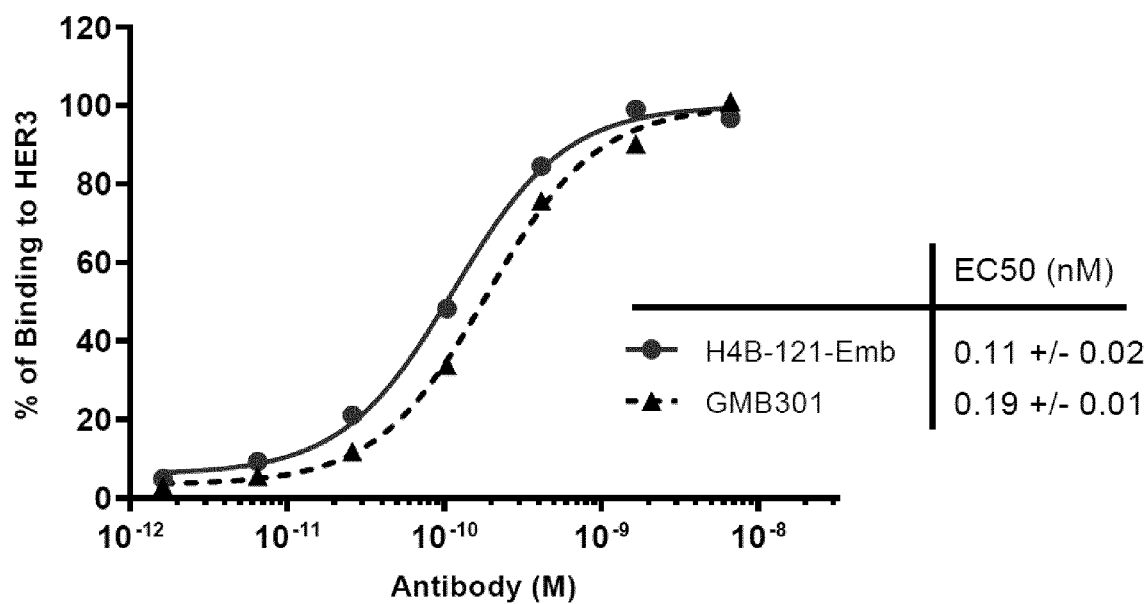

FIG. 5 shows the variation of % of binding to HER3 of antibodies H4B-121-emb and GMB301 in function of the concentration of said antibodies. The corresponding EC50 of the two antibodies is also indicated in nM.

Abscissa: Concentration of the antibody (M). Ordinate: % of binding to HER3.

Figure 6:
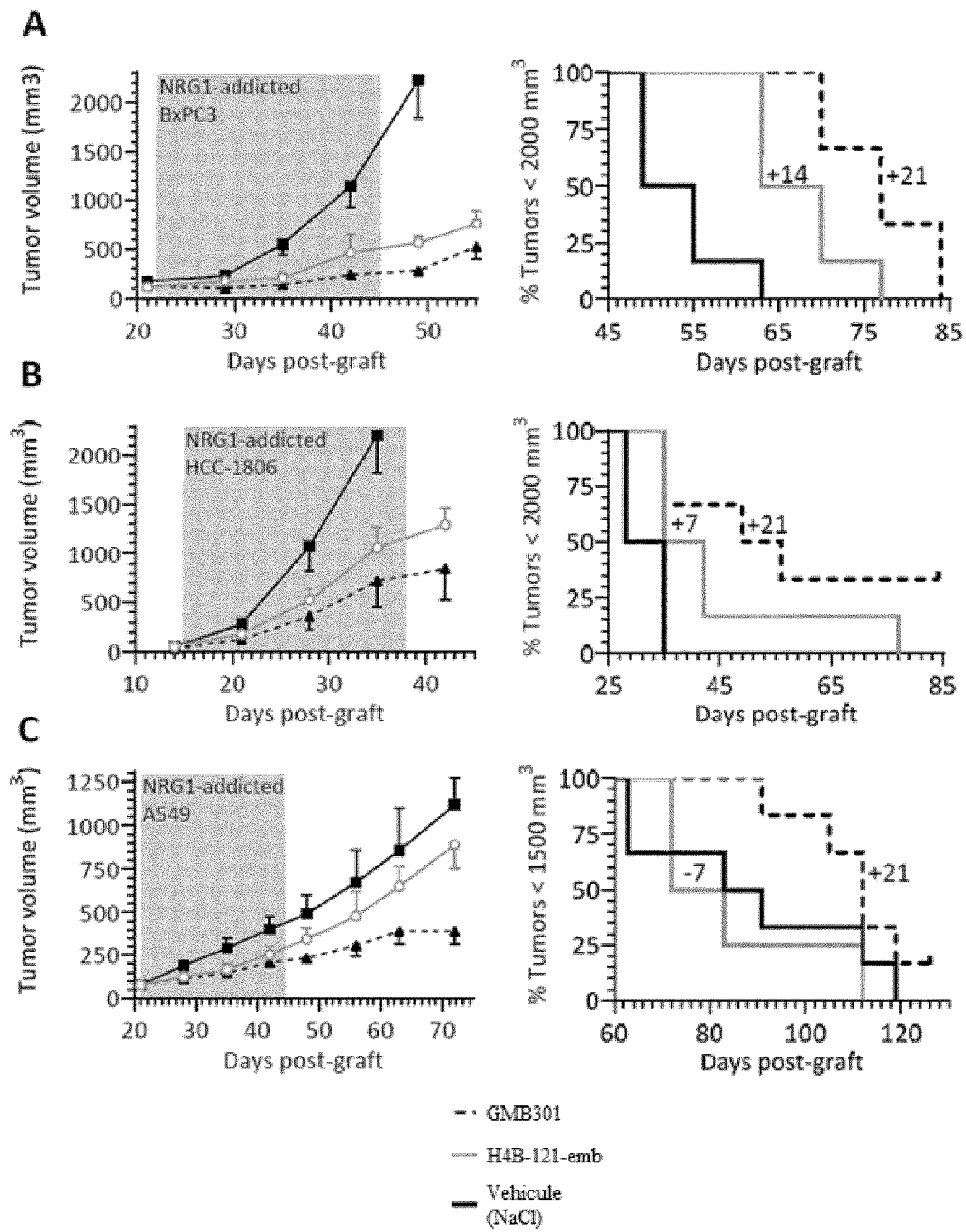

FIG. 6 shows the effect of a treatment with GMB301, the emabling version of the antibody H4B 121 (H4B-121-emb) or with vehicle (NaCl—negative control) on tumor volume of 3 different types of NRG1-addicted tumors over time (left panel) (FIG. 5A: NRG1-addicted pancreatic BxPC3 (3×106); FIG. 5B: triple-negative breast cancer HCC-1806 (1×106); and FIG. 5C: lung A549 cancer cells).

On the right panel, the corresponding gain in days of treatments are represented for the same treatment applied to the same different cancer types.

Tumor growth data (left panel) are presented as the mean tumor volume (mm$^3$)+/−S.E.M. for each group of nude mice varying with time (days). Grayed zone corresponds to the time of treatment. Kaplan-Meier survival curves were calculated when tumors reached a volume of 1500 or 2000 mm$^3$ and mice were sacrificed.

The benefit (gain in days of the treatment vs control group) (right panel) is indicated on the Kaplan-Meier curves.

Left panel: Abscissa: Tumor volume (mm³), and Ordinate: Days post-graft.

Right panel: Abscissa: % tumors<1500 mm³, and Ordinate: Days post-graft.

DETAILED DESCRIPTION OF THE INVENTION

The inventors have generated a chimeric low-fucose anti-human HER3 antibody, named GMB301, which comprises Complementary Determining Regions (CDRs) of the mouse antibody 9F7-F11 previously assayed by Lazrek et al (2013), which GMB301 antibody possesses unexpected properties as an anti-cancer agent.

The inventors have shown that a chimerized antibody having CDRs of the 9F7-F11 antibody used by Lazrek et al. (2013) and having a low fucose content possesses an increased in vivo anti-tumor activity, especially against NRG-expressing tumors.

Thus, the inventors have unexpectedly found that an antibody having a specific glycosylation pattern, and more precisely a low fucose content, as well as human constant domains, may behave as an anticancer agent differently from a parent mouse antibody having the same CDRs and a higher fucose content.

Surprisingly, the inventors have shown that the low fucose antibody that is described herein has specific tumor targeting activities, as compared with a parent antibody having the same CDRs, mouse constant domains and a higher fucose content.

The results obtained by the inventors are all the more surprising that, in contrast to what might have been expected, the said antibody having CDRs of the 9F7-F11 antibody, human constant domains and having a low fucose content does not exhibit an increased anti-tumor activity against tumors in the absence of NRG.

Thus, the inventors have unexpectedly found that the increased in vivo anti-tumor activity of the low fucose chimerized anti-HER3 antibody described herein does not seem to be mediated through enhanced ADCC or ADCP properties, but instead by (an) unknown and unexpected mechanism(s).

The anti-HER3 chimerized antibody having a low fucose content which is described herein possesses an improved antitumoral activity specifically against a population of tumors expressing HER3, in the presence of neuregulin, which encompasses an improved antitumoral activity specifically against a population of tumors expressing both HER3 and neuregulin (autocrine secretion), or that could be stimulated by neuregulin secreted by non-tumor cells from the microenvironment via a paracrine pathway.

The inventors have found that, as disclosed in the examples herein, and contrary to all expectations:

(i) in the absence of neuregulin in the tumor treated with GMB301, the activity of the said antibody against the tumor growth is similar to the one of 9F7-F11; and (ii) selectively in the presence of neuregulin at the site of the tumor considered, the anti-tumor activity of GMB301 is significantly higher than the anti-tumor activity of 9F7-F11.

The man skilled in the art would have expected from a low-fucose (emabling) version of a known antibody to work more efficiently that the wild type antibody. However, this is not the case in the present situation, as demonstrated in the examples of the invention.

It follows that the anti-HER3 chimerized low fucose antibody that is described herein provides at least the following advantages over the anti-HER3 antibodies described in the prior art:

- it is more efficient against autocrine or paracrine ligand-dependent tumors (due to its allosteric effect);
- it is more efficient when resistance, mediated by up-regulation of HER3 ligands, occurs;
- it may be used to treat conditions where existing therapeutic antibodies are clinically ineffective, such as against triple-negative breast cancer, pancreatic cancer, and other specific cancers (ex: renal cell carcinoma).

Definitions

The term "neuregulin" has its general meaning in the art and is often used interchangeably with the term "heregulin". The heregulin family includes alpha, beta and gamma heregulins (Holmes et al., Science, 256: 1205-1210 (1992); U.S. Pat. No. 5,641,869; and Schaefer et al. Oncogene 15: 1385-1394 (1997)); neu differentiation factors (NDFs), glial growth factors (GGFs); acetylcholine receptor inducing activity (ARIA); and sensory and motor neuron derived factor (SMDF). For a review, see Groenen et al. Growth Factors 11:235-257 (1994); Lemke, G. Molec. & Cell. Neurosci. 7:247-262 (1996) and Lee et al. Pharm. Rev. 47:51-85 (1995); Falls and D. (2003). "neuregulins: functions, forms, and signaling strategies." Experimental Cell Research 284(1): 14-30.

The term "HER3" refers to the human HER3 receptor as described in Plowman et al., Proc. Natl. Acad. Sci. USA, 87:4905-4909 (1990); see, also, Kani et al., Biochemistry 44: 15842-857 (2005), Cho and Leahy, Science 297: 1330-1333 (2002)). HER3 is also known as "HER3".

The term "anti-human-HER3 antibody" refers to an antibody directed against human HER3.

According to the present invention, "antibody" or "immunoglobulin" have the same meaning, and will be used equally in the present invention. The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also variants (including derivatives) of antibodies. In natural antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant.

Antibody combining sites are made up of residues that are primarily from the hypervariable or complementarity determining regions (CDRs). Occasionally, residues from non-hypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs.

The term "chimeric antibody" refers to an antibody which comprises a VH domain and a VL domain of an antibody which are derived from one species and the constant domain which is derived from another species, for example an antibody in which the variable region sequences are derived from a mouse antibody and the constant region sequences are derived from a human antibody.

According to the invention, the term "humanized antibody" refers to an antibody having variable region framework and constant regions from a human antibody but retains the mouse CDRs of antibody of the invention.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "treatment" or "therapy" refers to administering an active agent with the purpose to cure, heal, alleviate, relieve, alter, remedy, ameliorate, improve, or affect a condition (e.g., a disease), the symptoms of the condition, or to prevent or delay the onset of the symptoms, complications, biochemical indicia of a disease, or otherwise arrest or inhibit further development of the disease, condition, or disorder in a statistically significant manner.

According to the invention, the term "patient" or "patient in need thereof" is intended for a human or non-human mammal affected or likely to be affected with cancer associated with the expression of human HER3.

By a "therapeutically effective amount" of the antibody of the invention is meant a sufficient amount of the antibody to treat said cancer, at a reasonable benefit/risk ratio applicable to any medical treatment. It will be understood, however, that the total daily usage of the antibodies and compositions of the present invention will be decided by the attending physician within the scope of sound medical judgment. The specific therapeutically effective dose level for any particular patient will depend upon a variety of factors including the disorder being treated and the severity of the disorder; activity of the specific antibody employed; the specific composition employed, the age, body weight, general health, sex and diet of the patient; the time of administration, route of administration, and rate of excretion of the specific antibody employed; the duration of the treatment; drugs used in combination or coincidental with the specific antibody employed; and like factors well known in the medical arts. For example, it is well known within the skill of the art to start doses of the compound at levels lower than those required to achieve the desired therapeutic effect and to gradually increase the dosage until the desired effect is achieved.

As used herein, the percent identity between two amino acid sequences can be determined using the algorithm of E. Meyers and W. Miller (Comput. Appl. Biosci., 4:1 1-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. MoI, Biol. 48:444-453, 1970) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6.

Antibodies of the Invention

The present invention provides for neuregulin (NRG)-non competitive allosteric anti-HER3 antibodies, preferably in a purified form or in an isolated form.

Therefore, the invention relates to an anti-human-HER3 antibody comprising:

(a) a heavy chain wherein the variable domain comprises:
a H-CDR1 having a sequence set forth as SEQ ID NO: 2;
a H-CDR2 having a sequence set forth as SEQ ID NO: 3; and
a H-CDR3 having a sequence set forth as SEQ ID NO: 4; and (b) a light chain wherein the variable domain comprises at least a CDR having a sequence chosen from the group consisting of SEQ ID NO: 6 as L-CDR1, the amino acid sequence SAS as L-CDR2 and SEQ ID NO: 8 as L-CDR3;
said antibody having a human constant region; and
less than 65% of the glycan structures carried by the glycosylation site of the antibody comprise a fucose molecule.

The sequences of interest in the present application are indicated in the following Table 1:

TABLE 1 amino acid sequences of VH, VL, CDRs and full heavy and light chains of mAb GMB301

| mAb GMB301 Domains | Sequences |
|---|---|
| VH | EVKLVESGGGLVQPGGSLKLSCAASGFTFSSYTMSWVRQTPEK RLEWVAYISDGGGVTYYPDTIKGRFTISRDNAKNTLYLQMSSL KSEDTAMYYCARDRYGLFAYWGQGTLVTVSA (SEQ ID NO: 1) |
| H CDR1 | GFTFSSYT (SEQ ID NO: 2) |
| H CDR2 | ISDGGGVT (SEQ ID NO: 3) |
| H CDR3 | ARDRYGLFAY (SEQ ID NO: 4) |

TABLE 1-continued amino acid sequences of VH, VL, CDRs and full heavy and light chains of mAb GMB301

| mAb GMB301 Domains | Sequences |
|---|---|
| VL | DIVMTQSQKFMSTSVGDRVSITCKASQNVGIAVAWYQQKPGQS PKLLIYSASNRYTGVPDRFTGSGSGTDFTLTISNMQSEDLADYF CQQYSNYPYTFGGGTKLEIK (SEQ ID NO: 5) |
| L CDR1 | QNVGIA (SEQ ID NO: 6) |
| L CDR2 | SAS |
| L CDR3 | QQYSNYPYT (SEQ ID NO: 8) |
| HEAVY CHAIN | EVKLVESGGGLVQPGGSLKLSCAASGFTFSSYTMSWVRQTPEK RLEWVAYISDGGGVTYYPDTIKGRFTISRDNAKNTLYLQMSSL KSEDTAMYYCARDRYGLFAYWGQGTLVTVSAASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKKV EPKSCDKTHTCPPCPAPELLGGPSVFLFPPKPKDTLMISRTPEVT CVVVDVSHEDPEVKFNWYVDGVEVHNAKTKPREEQYNSTYR VVSVLTVLHQDWLNGKEYKCKVSNKALPAPIEKTISKAKGQPR EPQVYTLPPSRDELTKNQVSLTCLVKGFYPSDIAVEWESNGQPE NNYKTTPPVLDSDGSFFLYSKLTVDKSRWQQGNVFSCSVMHEA LHNHYTQKSLSLSPGK (SEQ ID NO: 9) |
| LIGHT CHAIN | DIVMTQSQKFMSTSVGDRVSITCKASQNVGIAVAWYQQKPGQS PKLLIYSASNRYTGVPDRFTGSGSGTDFTLTISNMQSEDLADYF CQQYSNYPYTFGGGTKLEIKRTVAAPSVFIFPPSDEQLKSGTASV VCLLNNFYPREAKVQWKVDNALQSGNSQESVTEQDSKDSTYS LSSTLTLSKADYEKHKVYACEVTHQGLSSPVTKSFNRGEC (SEQ ID NO: 10) |

According to an embodiment, the antibody of the invention comprises a light chain variable region comprising SEQ ID NO:6 as L-CDR1, the amino acid sequence SAS as L-CDR2 and SEQ ID NO:8 as L-CDR3.

According to a further embodiment, the heavy chain variable region of the antibody of the invention has the amino acid sequence set forth as SEQ ID NO: 1 and/or the light chain variable region has the amino acid sequence set forth as SEQ ID NO: 5. Preferably, the heavy chain variable region of said antibody has the amino acid sequence set forth as SEQ ID NO: 1 and the light chain variable region has the amino acid sequence set forth as SEQ ID NO: 5.

According to another embodiment, the heavy chain of the antibody of the invention has the amino acid sequence set forth as SEQ ID NO: 9 and/or the light chain of said antibody has the amino acid sequence set forth as SEQ ID NO: 10. Preferably, the heavy chain of said antibody has the amino acid sequence set forth as SEQ ID NO: 9 and the light chain of said antibody has the amino acid sequence set forth as SEQ ID NO: 10.

According to a further embodiment, an antibody according to the invention is such that less than 50% of the glycan structures carried by the glycosylation site of the antibody comprise a fucose molecule, preferably less than 40%, more preferably less than 30%, in particular less than 20%.

According to a particular embodiment, the antibody of the invention is a chimeric antibody, preferably a chimeric mouse/human antibody, in particular a humanized antibody.

Methods of Producing Antibodies of the Invention

Anti-human-HER3 antibodies of the invention may be produced by any technique known in the art, such as, without limitation, any chemical, biological, genetic or enzymatic technique, either alone or in combination.

Knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies of the invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

Nucleic Acid Sequence

Accordingly, a further object of the invention relates to a nucleic acid sequence encoding an antibody according to the invention.

Typically, said nucleic acid is a DNA or RNA molecule, which may be included in any suitable vector, such as a plasmid, cosmid, episome, artificial chromosome, phage or a viral vector.

Vectors

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

So, a further object of the invention relates to a vector comprising a nucleic acid of the invention.

Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason JO et al. 1985) and enhancer (Gillies S D et al. 1983) of immunoglobulin H chain and the like.

Any expression vector for animal cell can be used, so long as a gene encoding the human antibody C region can be inserted and expressed. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like.

Other examples of plasmids include replicating plasmids comprising an origin of replication, or integrative plasmids, such as for instance pUC, pcDNA, pBR, and the like.

Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. No. 5,882,877, U.S. Pat. No. 6,013,516, U.S. Pat. No. 4,861,719, U.S. Pat. No. 5,278,056 and WO 94/19478.

Host Cells

A further object of the present invention relates to a host cell which has been transfected, infected or transformed by a nucleic acid and/or a vector according to the invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA bas been "transformed".

The nucleic acids of the invention may be used to produce an antibody of the invention in a suitable expression system. The term "expression system" means a host cell and compatible vector under suitable conditions, e.g. for the expression of a protein coded for by foreign DNA carried by the vector and introduced to the host cell.

Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse 5P2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag.20 cell (ATCC CRL1662, hereinafter referred to as "YB2/0 cell"), and the like.

Chimeric Antibodies

In a particular embodiment, a human chimeric antibody of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell.

As the CH domain of a human chimeric antibody, it may be any region which belongs to human immunoglobulin, but those of IgG class are suitable and any one of subclasses belonging to IgG class, such as IgG1, IgG2, IgG3 and IgG4, can also be used. Also, as the CL of a human chimeric antibody, it may be any region which belongs to Ig, and those of kappa class or lambda class can be used.

Methods for producing chimeric antibodies involve conventional recombinant DNA and gene transfection techniques are well known in the art (See Morrison S L. et al. (1984) and patent documents U.S. Pat. No. 5,202,238; and U.S. Pat. No. 5,204,244).

According to a preferred embodiment, the antibodies of the present invention are humanized.

Function-Conservative Variants

A further object of the present invention also encompasses function-conservative variants of the antibodies of the present invention.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared.

Two amino acid sequences are "substantially homologous" or "substantially similar" when greater than 80%, preferably greater than 85%, preferably greater than 90% of the amino acids are identical, or greater than about 90%, preferably greater than 95%, are similar (functionally identical) over the whole length of the shorter sequence. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences of the invention, or corresponding DNA sequences which encode said antibodies, without appreciable loss of their biological activity.

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Glycosylation

The glycosylation of the antibodies of the invention is altered in view of its fucose content.

Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site.

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr H. et al. (1987) and by Edge, A S. et al. (1981). Enzymatic cleavage of carbohydrate moieties on antibodies can be achieved by the use of a variety of endo-and exo-glycosidases as described by Thotakura, N R. et al. (1987).

More particularly, the glycosylation of the antibodies of the invention is altered in that less than 65% of the glycan structures carried by the glycosylation site of the antibody comprise a fucose molecule.

Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation.

For example, EP1176195 by Hang et al. describes a cell line with a functionally disrupted FUT8 gene, which encodes a fucosyl transferase, such that antibodies expressed in such a cell line exhibit hypofucosylation or are devoid of fucosyl residues.

PCT Publication WO03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740).

Moreover, U.S. Pat. No. 7,931,895 and WO 01/77181 describe the production of low fucose antibodies produced in the YB2/0 cell line (ATCC®, reference CRL-1662).

Eureka Therapeutics further describes genetically engineered CHO mammalian cells capable of producing antibodies with altered mammalian glycosylation pattern devoid of fucosyl residues (http://www.eurekainc.com/a&boutus/companyoverview.html).

Alternatively, the antibodies of the invention can be produced in yeasts or filamentous fungi engineered for mammalian-like glycosylation pattern and capable of producing antibodies lacking fucose as glycosylation pattern (see for example EP1297172B1).

Antibody Assays

All these antibodies may be assayed for specific binding by any method known in the art. Many different competitive binding assay format(s) can be used for epitope binding. The immunoassays which can be used include, but are not limited to, competitive assay systems using techniques such western blots, radioimmunoassays, ELISA, "sandwich" immunoassays, immunoprecipitation assays, precipitin assays, gel diffusion precipitin assays, immunoradiometric assays, fluorescent immunoassays, protein A immunoassays, and complement-fixation assays. Such assays are routine and well known in the art (see, e.g., Ausubel et al., eds, 1994 Current Protocols in Molecular Biology, Vol. 1, John Wiley & sons, Inc., New York). For example, the BIACORE® (GE Healthcare, Piscaataway, N.J.) is one of a variety of surface plasmon resonance assay formats that are routinely used to epitope bin panels of monoclonal antibodies. Additionally, routine cross-blocking assays such as those described in Antibodies, A Laboratory Manual, Cold Spring Harbor Laboratory, Ed Harlow and David Lane, 1988, can be performed.

Immunoconjugates

Detectable Label

An antibody of the invention can be conjugated with a detectable label to form an anti-HER3 immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below.

The detectable label can be a radioisotope that is detected by autoradiography. Isotopes that are particularly useful for the purpose of the present invention are $^3H$, $^{125}I$, $^{131}I$, $^{35}S$ and $^{14}C$.

Anti-HER3 immunoconjugates of the invention can also be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

Alternatively, anti-HER3 immunoconjugates of the invention can be detectably labeled by coupling an antibody to a chemiluminescent compound. The presence of the chemiluminescent-tagged immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label anti-HER3 immunoconjugates of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, anti-HER3 immunoconjugates can be detectably labeled by linking an anti-human-HER3 monoclonal antibody to an enzyme. When the anti-HER3-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels which can be employed in accordance with the present invention. The binding of marker moieties to anti-human-HER3 monoclonal antibodies can be accomplished using standard techniques known to the art. Typical methodology in this regard is described by Kennedy et al., *Clin. Chim. Acta* 70:1, 1976; Schurs et al., *Clin. Chim. Acta* 81:1, 1977; Shih et al., *Int'l J. Cancer* 46:1101, 1990; Stein et al., *Cancer Res.* 50:1330, 1990; and Coligan, supra.

Moreover, the convenience and versatility of immunochemical detection can be enhanced by using anti-human-HER3 monoclonal antibodies that have been conjugated with avidin, streptavidin, and biotin. (See, e.g., Wilchek et al. (eds.), "Avidin-Biotin Technology," *Methods In Enzymology* (Vol. 184) (Academic Press 1990); Bayer et al., "Immunochemical Applications of Avidin-Biotin Technology," in *Methods In Molecular Biology* (Vol. 10) 149-162 (Manson, ed., The Humana Press, Inc. 1992).)

Methods for performing immunoassays are well-established. (See, e.g., Cook and Self, "Monoclonal Antibodies in Diagnostic Immunoassays," in *Monoclonal Antibodies: Production, Engineering, and Clinical Application* 180-208 (Ritter and Ladyman, eds., Cambridge University Press 1995); Perry, "The Role of Monoclonal Antibodies in the Advancement of Immunoassay Technology," in *Monoclonal Antibodies: Principles and Applications* 107-120 (Birch and Lennox, eds., Wiley-Liss, Inc. 1995); Diamandis, *Immunoassay* (Academic Press, Inc. 1996).)

Antibody-Drug Conjugates (ADC)

In another aspect, the present invention provides an anti-human-HER3 monoclonal antibody-drug conjugate. An "anti-human-HER3 monoclonal antibody-drug conjugate" as used herein refers to an anti-human-HER3 monoclonal antibody according to the invention conjugated to a therapeutic agent.

Such anti-human-HER3 monoclonal antibody-drug conjugates (ADC) produce clinically beneficial effects on HER3-expressing cells when administered to a subject, such as, for example, a subject with a HER3-expressing cancer, typically when administered alone but also in combination with other therapeutic agents.

In typical embodiments, an anti-human-HER3 monoclonal antibody is conjugated to a cytotoxic agent, such that the resulting antibody-drug conjugate (ADC) exerts a cytotoxic or cytostatic effect on a HER3-expressing cell (e.g., a HER3-expressing cancer cell) when taken up or internalized by the cell. Particularly suitable moieties for conjugation to antibodies are chemotherapeutic agents, prodrug converting enzymes, radioactive isotopes or compounds, or toxins. For example, an anti-human-HER3 monoclonal antibody can be conjugated to a cytotoxic agent such as a chemotherapeutic agent or a toxin (e.g., a cytostatic or cytocidal agent such as, for example, abrin, ricin A, pseudomonas exotoxin, or diphtheria toxin).

Useful classes of cytotoxic agents include, for example, antitubulin agents, auristatins, DNA minor groove binders, DNA replication inhibitors, alkylating agents (e.g., platinum complexes such as cis-platin, mono(platinum), bis(platinum) and tri-nuclear platinum complexes and-carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, or the like.

Individual cytotoxic agents include, for example, an androgen, anthramycin (AMC), asparaginase, 5-azacytidine, azathioprine, bleomycin, busulfan, buthionine sulfoximine, camptothecin, carboplatin, carmustine (BSNU), CC-1065 (Li et al., *Cancer Res.* 42:999-1004, 1982), chlorambucil, cisplatin, colchicine, cyclophosphamide, cytarabine, cytidine arabinoside, cytochalasin B, dacarbazine, dactinomycin (formerly actinomycin), daunorubicin, decarbazine, docetaxel, doxorubicin, an estrogen, 5-fluordeoxyuridine, etopside phosphate (VP-16), 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbizine, streptozotocin, tenoposide (VM-26), 6-thioguanine, thioTEPA, topotecan, vinblastine, vincristine, and vinorelbine.

Particularly suitable cytotoxic agents include, for example, dolastatins (e.g., auristatin E, AFP, MMAF, MMAE), DNA minor groove binders (e.g., enediynes and lexitropsins), duocarmycins, taxanes (e.g., paclitaxel and docetaxel), puromycins, vinca alkaloids, CC-1065, SN-38 (7-ethyl-10-hydroxy-camptothein), topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, and mitoxantrone.

In certain embodiments, a cytotoxic agent is a conventional chemotherapeutic such as, for example, doxorubicin, paclitaxel, melphalan, vinca alkaloids, methotrexate, mitomycin C or etoposide. In addition, potent agents such as CC-1065 analogues, calicheamicin, maytansine, analogues of dolastatin 10, rhizoxin, and palytoxin can be linked to an anti-HER3-expressing antibody.

In specific variations, the cytotoxic or cytostatic agent is auristatin E (also known in the art as dolastatin-10) or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP (dimethylvaline-valine-dolaisoleuine-dolaproine-phenylalanine-p-phenylenediamine), MMAF (dovaline-valine-dolaisoleunine-dolaproine-phenylalanine), and MAE (monomethyl auristatin E). The synthesis and structure of auristatin E and its derivatives are described in U.S. Patent Application Publication No. 20030083263; International Patent Publication Nos. WO 2002/088172 and WO 2004/010957; and U.S. Pat. Nos. 6,884,869; 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

In other variations, the cytotoxic agent is a DNA minor groove binding agent. (See, e.g., U.S. Pat. No. 6,130,237.) For example, in certain embodiments, the minor groove binding agent is a CBI compound. In other embodiments, the minor groove binding agent is an enediyne (e.g., calicheamicin).

In certain embodiments, an antibody-drug conjugate (ADC) comprises an anti-tubulin agent. Examples of anti-tubulin agents include, for example, taxanes (e.g., Taxol® (paclitaxel), Taxotere® (docetaxel)), T67 (Tularik), vinca alkyloids (e.g., vincristine, vinblastine, vindesine, and vinorelbine), and dolastatins (e.g., auristatin E, AFP, MMAF, MMAE, AEB, AEVB). Other antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin. In some embodiments, the cytotoxic agent is a maytansinoid, another group of anti-tubulin agents. For example, in specific embodiments, the maytansinoid is maytansine or DM-1 (ImmunoGen, Inc.; see also Chari et al., *Cancer Res.* 52:127-131, 1992).

In other embodiments, the cytotoxic agent is an antimetabolite. The antimetabolite can be, for example, a purine antagonist (e.g., azothioprine or mycophenolate mofetil), a dihydrofolate reductase inhibitor (e.g., methotrexate), acyclovir, gangcyclovir, zidovudine, vidarabine, ribavarin, azidothymidine, cytidine arabino side, amantadine, dideoxyuridine, iododeoxyuridine, poscarnet, or trifluridine.

In other embodiments, an anti-human-HER3 monoclonal antibody is conjugated to a pro-drug converting enzyme. The pro-drug converting enzyme can be recombinantly fused to the antibody or chemically conjugated thereto using known methods. Exemplary pro-drug converting enzymes are carboxypeptidase G2, β-glucuronidase, penicillin-V-amidase, penicillin-G-amidase, β-lactamase, β-glucosidase, nitroreductase and carboxypeptidase A.

Techniques for conjugating therapeutic agents to proteins, and in particular to antibodies, are well-known. (See, e.g., Arnon et al., "Monoclonal Antibodies For Immunotargeting Of Drugs In Cancer Therapy," in *Monoclonal Antibodies And Cancer Therapy* (Reisfeld et al. eds., Alan R. Liss, Inc., 1985); Hellstrom et al., "Antibodies For Drug Delivery," in *Controlled Drug Delivery* (Robinson et al. eds., Marcel Deiker, Inc., 2nd ed. 1987); Thorpe, "Antibody Carriers Of Cytotoxic Agents In Cancer Therapy: A Review," in *Monoclonal Antibodies '84: Biological And Clinical Applications* (Pinchera et al. eds., 1985); "Analysis, Results, and Future Prospective of the Therapeutic Use of Radiolabeled Antibody In Cancer Therapy," in *Monoclonal Antibodies For Cancer Detection And Therapy* (Baldwin et al. eds., Academic Press, 1985); and Thorpe et al., 1982, *Immunol. Rev.* 62:119-58. See also, e.g., PCT publication WO 89/12624.).

Linkers

Typically, the antibody-drug conjugate compounds comprise a linker unit between the drug unit and the antibody unit. In some embodiments, the linker is cleavable under intracellular conditions, such that cleavage of the linker releases the drug unit from the antibody in the intracellular environment. In yet other embodiments, the linker unit is not cleavable and the drug is released, for example, by antibody degradation.

In some embodiments, the linker is cleavable by a cleaving agent that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123).

Most typical are peptidyl linkers that are cleavable by enzymes that are present in 191P4D12-expressing cells. Examples of such linkers are described, e.g., in U.S. Pat. No. 6,214,345, incorporated herein by reference in its entirety and for all purposes. In a specific embodiment, the peptidyl linker cleavable by an intracellular protease is a Val-Cit linker or a Phe-Lys linker (see, e.g., U.S. Pat. No. 6,214,345, which describes the synthesis of doxorubicin with the Val-Cit linker). One advantage of using intracellular proteolytic release of the therapeutic agent is that the agent is typically attenuated when conjugated and the serum stabilities of the conjugates are typically high.

In other embodiments, the cleavable linker is pH-sensitive, i.e., sensitive to hydrolysis at certain pH values.

Typically, the pH-sensitive linker hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In yet other embodiments, the linker is cleavable under reducing conditions (e.g., a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene), SPDB and SMPT. (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In yet other embodiments, the linker unit is not cleavable and the drug is released by antibody degradation.

Typically, the linker is not substantially sensitive to the extracellular environment. As used herein, "not substantially sensitive to the extracellular environment," in the context of a linker, means that no more than about 20%, typically no more than about 15%, more typically no more than about 10%, and even more typically no more than about 5%, no more than about 3%, or no more than about 1% of the linkers, in a sample of antibody-drug conjugate compound, are cleaved when the antibody-drug conjugate compound is present in an extracellular environment (e.g., in plasma). Whether a linker is not substantially sensitive to the extracellular environment can be determined, for example, by incubating with plasma the antibody-drug conjugate compound for a predetermined time period (e.g., 2, 4, 8, 16, or 24 hours) and then quantitating the amount of free drug present in the plasma.

Therapeutic Uses

Antibodies or immunoconjugates, in particular antibody-drug conjugate, of the invention may be useful for treating any HER3-expressing cancer. The antibodies of the invention may be used alone or in combination with any suitable agent.

Examples of HER3-expressing cancer include but are not limited to, carcinoma, lymphoma, blastoma, sarcoma, and leukemia.

More particular examples of such cancers include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, melanoma, colorectal cancer, endometrial carcinoma, salivary gland carcinoma, kidney cancer, renal cancer, prostate cancer, vulval cancer, thyroid cancer, hepatic carcinoma and various types of head and neck cancer.

They are preferably chosen among breast cancer, ovarian cancer, small-cell lung cancer, non-small cell lung cancer, melanoma, pancreatic cancer and colorectal cancer, and more particularly among breast cancer, ovarian cancer and pancreatic cancer.

In one particular embodiment, a cancer treated using the methods of the present invention is breast cancer or ovarian cancer.

The present invention discloses a method for treating a cancer associated with the expression of HER3 comprising administering a subject in need thereof with a therapeutically effective amount of an antibody or immunoconjugate of the invention.

The antibodies and immunoconjugates of the invention are more particularly effective for treating a cancer associated with the expression of HER3 wherein neuregulin is present, in particular neuregulin 1β.

Thus, an object of the present invention is an antibody, and/or an immunoconjugate, according to the invention for its use in the treatment of a cancer associated with the expression of HER3 wherein neuregulin is present, in particular neuregulin 1β, in a subject.

In an embodiment, the antibodies and immunoconjugates of the invention are particularly suitable for the treatment of ligand (i.e. NRG) dependent cancers.

In an embodiment, the antibodies of the invention are particularly suitable for the treatment of autocrine or paracrine ligand-dependent tumors (due to its allosteric effect).

Accordingly, in an embodiment of the invention, the neuregulin present is secreted by the tumor and/or by the tissues and/or organs surrounding the tumor.

In some embodiment, the antibodies and immunoconjugates of the invention are particularly suitable for the treatment of cancers that are resistant to the treatment with antibodies, tyrosine kinase inhibitors (TKI), chemotherapeutic agents or anti-hormone agents.

In some embodiments, the antibodies of the invention are particularly suitable for the treatment of cancers selected from the group consisting of triple-negative breast cancer, pancreatic cancer, and renal cell carcinomas.

In certain embodiments, an anti-human-HER3 monoclonal antibody or immunoconjugate, in particular antibody-drug conjugate, is used in combination with a second agent for treatment of a disease or disorder.

When used for treating cancer, an anti-human-HER3 monoclonal antibody or immunoconjugate of the present invention may be used in combination with conventional cancer therapies such as, e.g., surgery, radiotherapy, chemotherapy, or combinations thereof.

In certain aspects, other therapeutic agents useful for combination cancer therapy with an anti-HER3 antibody or antibody-drug conjugate in accordance with the present invention include anti-angiogenic agents.

In some aspects, an antibody or antibody-drug conjugate in accordance with the present invention is co-administered with a cytokine (e.g., a cytokine that stimulates an immune response against a tumor).

In some other aspects, other therapeutic agents useful for combination therapy include an antagonist of certain factors that are involved in tumor growth such as, for example, EGFR, HER2, or HER4.

In one particular embodiment, an anti-human-HER3 monoclonal antibody or immunoconjugate, in particular antibody-drug conjugate, of the present invention is used in combination with an anti-human-HER2 monocolonal antibody, such as Trastuzumab or Pertuzumab.

In some embodiments, an anti-human-HER3 monoclonal antibody or immunoconjugate, in particular antibody-drug conjugate, as described herein is used in combination with a tyrosine kinase inhibitor (TKI). BAY 43-9006 (sorafenib, Nexavar®) and SU11248 (sunitinib, Sutent®) are two such TKIs that have been approved. Other TKIs include, but are not limited to: Imatinib mesylate (Gleevec®, Novartis); Gefitinib (Iressa®, AstraZeneca); Erlotinib hydrochloride (Tarceva®, Genentech); Vandetanib (Zactima®, AstraZeneca), Tipifarnib (Zarnestra®, Janssen-Cilag); Dasatinib (Sprycel®, Bristol Myers Squibb); Lonafarnib (Sarasar®, Schering Plough); Vatalanib succinate (Novartis, Schering AG); Lapatinib (Tykerb®, GlaxoSmithKline); Nilotinib (Novartis); Lestaurtinib (Cephalon); Pazopanib hydrochloride (GlaxoSmithKline); Axitinib (Pfizer); Canertinib dihydrochloride (Pfizer); Pelitinib (National Cancer Institute, Wyeth); Tandutinib (Millennium); Bosutinib (Wyeth); Semaxanib (Sugen, Taiho); AZD-2171 (AstraZeneca); VX-680 (Merck, Vertex); EXEL-0999 (Exelixis); ARRY-142886 (Array BioPharma, AstraZeneca); PD-0325901 (Pfizer); AMG-706 (Amgen); BIBF-1120 (Boehringer Ingelheim); SU-6668 (Taiho); CP-547632 (OSI); (AEE-788 (Novartis); BMS-582664 (Bristol-Myers Squibb); JNK-401 (Celgene); R-788 (Rigel); AZD-1152 HQPA (AstraZeneca); NM-3 (Genzyme Oncology); CP-868596 (Pfizer); BMS-599626 (Bristol-Myers Squibb); PTC-299 (PTC Therapeutics); ABT-869 (Abbott); EXEL-2880 (Exelixis); AG-024322 (Pfizer); XL-820 (Exelixis); OSI-930 (OSI); XL-184 (Exelixis); KRN-951 (Kirin Brewery); CP-724714 (OSI); E-7080 (Eisai); HKI-272 (Wyeth); CHIR-258 (Chiron); ZK-304709 (Schering AG); EXEL-7647 (Exelixis); BAY-57-9352 (Bayer); BIBW-2992 (Boehringer Ingelheim); AV-412 (AVEO); YN-968D1 (Advenchen Laboratories); Midostaurin (Novartis); Perifosine (AEterna Zentaris, Keryx, National Cancer Institute); AG-024322 (Pfizer); AZD-1152 (AstraZeneca); ON-01910Na (Onconova); and AZD-0530 (AstraZeneca).

Pharmaceutical Compositions

For administration, the anti-human-HER3 monoclonal antibody or antibody-drug conjugate of the invention is formulated as a pharmaceutical composition.

A pharmaceutical composition comprising an anti-human-HER3 monoclonal antibody or antibody-drug conjugate can be formulated according to known methods to prepare pharmaceutically useful compositions, whereby the therapeutic molecule is combined in a mixture with a pharmaceutically acceptable carrier.

A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. (See, e.g., Gennaro (ed.), Remington's Pharmaceutical Sciences (Mack Publishing Company, 19th ed. 1995).) Formulations may further include one or more excipients, preservatives, solubilizers, buffering agents, albumin to prevent protein loss on vial surfaces, etc.

Ways of Administration

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, parenteral, intranasal, intravenous, intramuscular, subcutaneous or intraocular administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the antibody may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Carriers

An antibody of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antibodies of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g. tablets or other solids for oral administration; time release capsules; and any other form currently used.

In certain embodiments, the use of liposomes and/or nanoparticles is contemplated for the introduction of antibodies into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 µm) are generally designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 µm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

Kits

Finally, the invention also provides kits comprising at least one antibody of the invention. Kits containing antibodies of the invention find use in detecting HER3 expression, or in therapeutic or diagnostic assays. Kits of the invention can contain an antibody coupled to a solid support, e.g., a tissue culture plate or beads (e.g., sepharose beads). Kits can be provided which contain antibodies for detection and quantification of HER3 in vitro, e.g. in an ELISA or a Western blot. Such antibody useful for detection may be provided with a label such as a fluorescent or radio label.

The invention will be further illustrated by the following figures and examples. However, these examples and figures should not be interpreted in any way as limiting the scope of the present invention.

Example 1: Generation and Production of GMB301

Low-fucose chimerized antibody GMB301 was obtained by sub-cloning of the VH and VL DNA sequences of parental 9F7-F11 antibody downstream to human Cg1 and Ck genes into mammalian expression vector. Such low fucose antibody was substantially produced in the YB2/0 cell line (ATCC®, reference CRL-1662).

Briefly, the VH-CH1-CH2-CH3 gamma chain isotype 1 and VL-Ckappa DNA sequences were constructed by gene synthesis (Geneart®) with codons optimization. The neo-synthetized heavy chain and light chain were subcloned into pMGM09-H and pMGM09-Lk vectors for each antibody chain expression.

These mammalian expression vectors permit the expression of the antibody in IgG1 format isotype driven by a CMV promoter. The YB2/0 cells were transfected for the generation of stable pools and a batch production was carried out over one week.

Example 2: GMB301 Binds to HER3 Extracellular Domain with High Affinity

GMB301 was incubated for 1 hour at 37° C. in Max-isorp® plates (Nunc) coated wells with 50 ng human HER3-Fc (recombinant HER3 extracellular domain Fc fusion, R&D systems).

The GMB301 concentrations used were in the range of 3.3 nM to 6.5 pM.

Bound GMB301 antibody were detected by a conjugated HRP-F(ab')2 goat anti human IgG F(ab')2 specific (Interchim). After two hours at 37° C. and three washes with PBS-Tween$_{20}$0.5%, TMB (3,3,5,5-tetramethylbenzidine, Sigma) was used as substrate for detecting HRP activity and 1M H$_2$SO$_4$ was added to stop the reaction and plate was read at 450 nm.

Figure 1:
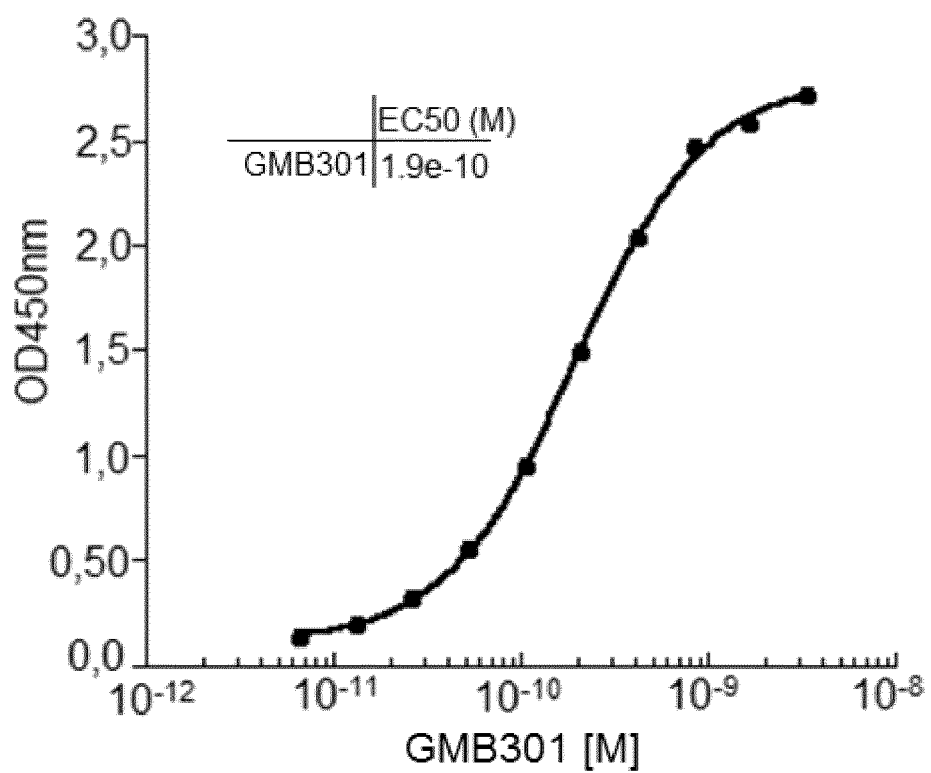
FIG. 1 shows the dose-effect curves obtained by ELISA assay for GMB301 of the invention in order to characterize its affinity to HER3. The ELISA assay was performed as described in Example 2. X-coordinate: Concentration of GMB301. Y-coordinate: Absorbance at OD 450 nm.

As depicted in FIG. 1, the GMB301 antibody exhibits a subnanomolar affinity (EC50 0.19 nM) to HER3 extracellular domain.

Example 3: In Vivo Effects of GMB301 on Reduction of Tumor Growth in Mice Xenografted with a Pancreatic Cancer Cell Line and Comparison with 9F7-F11

A. Athymic, 6- to 8-week-old, female BALB/c nude were purchased from Janvier and Charles Rivers Laboratories. EGFR$^{high}$, HER2/3$^{low}$, PTEN/PIK3CA wt, NRG$^{negative}$ and KRAS/BRAF-mutated NRG1β-independent pancreatic cancer cells HPAC (3×10$^6$) were injected s.c. into the right flank of athymic BALB/c nude mice. HPAC does not secrete the ligand NRG1β. All in vivo experiments were done in compliance with the French guidelines for experimental animal studies (Agreement no. B34-172-27).

Tumor-bearing mice were randomized in the different treatment groups when the tumors reached an approximate volume of 150 mm$^3$. The mice were treated by i.p. injections of GMB301 vs antibody 9F7-F11 vs vehicle (PBS). The amount of injected antibody was 300 µg/injection (15 mg/kg), twice a week, for 4 weeks consecutively (Q3D-4W). Tumor dimensions were measured weekly with a caliper and the volumes were calculated by the formula D1×D2×D3/2.

Figure 2:
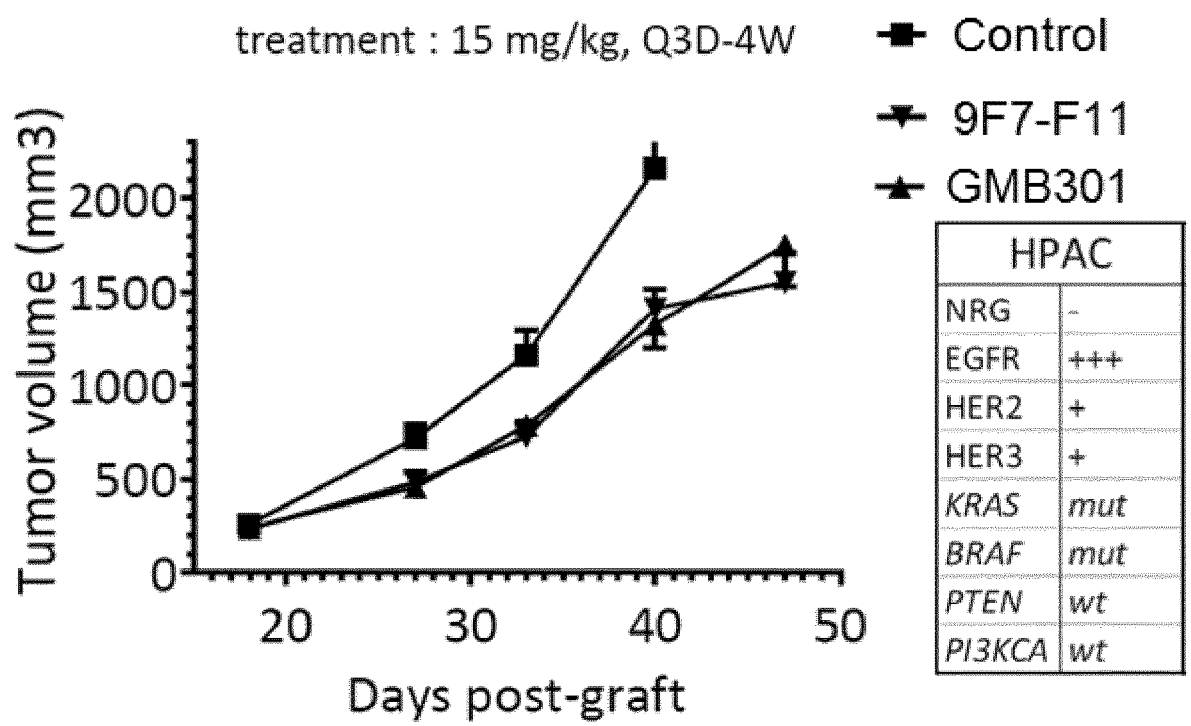
FIG. 2 shows the in vivo effects of a treatment with either GMB301, 9F7-F11 or PBS (control) of athymic, 6- to 8-week-old, female BALB/c nude injected with pancreatic cancer cells HPAC (EGFR$^{high}$, HER2/3$^{low}$, PTEN/PIK3CA wt, NRG$^{negative}$ and KRAS/BRAF-mutated, NRG1β-independent). 15 mg/kg is injected twice a week for 4 weeks consecutively (Q3D-4W). Tumor volumes are indicated in ordinate and were calculated by the formula D1×D2×D3/2.

As shown in FIG. 2, a significant reduction of HPAC tumor growth is observed in GMB301-treated mice with regard to mean tumor size measured in mice treated with vehicle. Surprisingly, similar results are observed in 9F7-F11-treated mice. Indeed, no significant difference is observed in the reduction of tumor growth with the two types of antibodies.

B. A protocol similar to the one of Point A has been performed, except that the pancreatic cancer cell line injected in the flank of athymic BALB/c nude mice is EGFR$^{high}$, HER2/3$^{high}$, KRAS/BRAF/PTEN/PIK3CA wt, NRG$^{positive}$ NRG1β-dependent pancreatic cancer cells BxPC3 (3×10$^6$). BxPC3 expressed HER3 receptor at low level (around 10,000 receptors/cell) and secreted the ligand NRG1β (NRG1β-dependent paracrine model).

Figure 3:
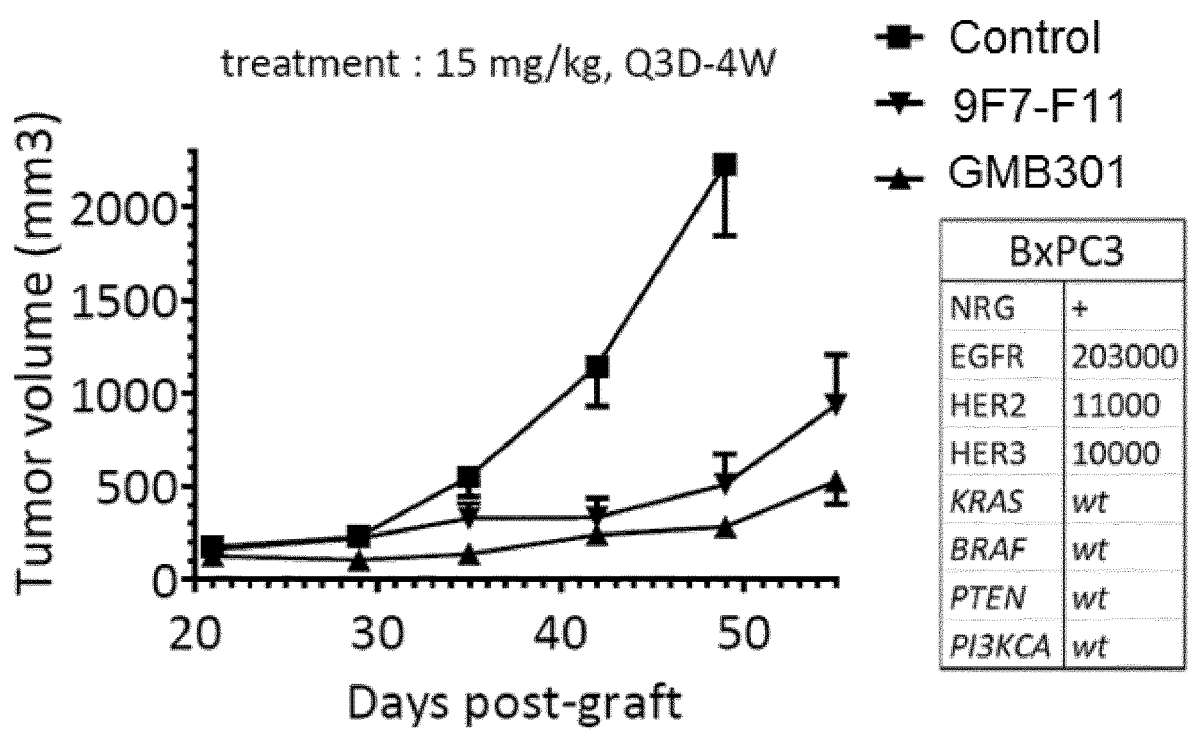
FIG. 3 shows the in vivo effects of a treatment with either GMB301, 9F7-F11 or PBS (control) of athymic, 6- to 8-week-old, female BALB/c nude injected with pancreatic cancer cells BxPC3 (EGFR$^{high}$, HER2/3$^{low}$, KRAS/BRAF/PTEN/PIK3CA wt, NRG$^{positive}$, NRG1β-dependent). 15 mg/kg is injected twice a week for 4 weeks consecutively (Q3D-4W). Tumor volumes are indicated in ordinate and were calculated by the formula D1×D2×D3/2.

As shown in FIG. 3, a strong reduction of BxPC3 tumor growth is observed in GMB301-treated mice with regard to mean tumor size measured in mice treated with vehicle.

This time however, a lower reduction of mean tumor size was observed in the mouse group treated with 9F7-F11 compared to the reduction observed in GMB301-treated mice. Better efficiency of GMB301 with regard to 9F7-F11 was visible as soon as 29 days post-tumor implantation.

Taken together, these results demonstrate that GMB301 delayed tumor growth more efficiently than 9F7-F11 in mice xenografted with NRG1β secretor cancer, but that similar results are obtained when comparing the effectiveness of GMB301 and 9F7-F11 in mice xenografted with non-NRG1β secretor cancer.

The inventors have thus identified an antibody which is effective against NRG-dependent and independent cancers, with a superior effectiveness compared to known anti-HER3 antibodies in cancers where the natural ligand NRG is expressed.

Example 4: GMB301 ADCC on Tumor Cells Compared to H4B-121 Emabling

The H4B-121 emabling (H4B-121-emb) was produced in YB2/0 cell line according to the Emabling® Technology from LFB, which led to the generation of low-fucose H4B-121.

ADCC was conducted using the Cytotox 96 Non-radioactive cytotoxicity assay (Promega) which measured the release of lactate dehydrogenase (LDH) from damaged cells.

The target cells (T) from breast carcinoma MDA-MB-453 were cultivated in DMEM+10% FCS+antibiotics and collected with trypsin/EDTA in exponential growth phase.

After a washing step and checking cell number and viability, 20,000 MDA-MB-453 cells were added to each well of sterile flat-bottom 96-well plates, and pre-incubated for 24 h at 37° C., 5% CO2.

1 µg/ml of the tested antibodies (GMB301, H4B-121-emb and irrelevant control antibody (Px)) was then incubated to target cells MDA-MB-453, with NRG1β (100 ng/ml), 30 minutes before adding effector cells. (Triplicate)

Peripheral blood mononuclear cells (PBMC) from healthy donors were prepared as effector cells (E) by density gradient centrifugation (Ficoll-Paque; d=1.077; GE Healthcare) according to the manufacturer's protocol. The cell number of PBMC was adjusted to $6 \times 10^6$ cells/ml and 300,000 effector cells were added to each well (15:1 E:T ratio).

The following controls were set up for each experiment: target cells alone (target spontaneous LDH release), PBMCs alone (effector spontaneous LDH release), target cells with PBMC (antibody-independent LDH release), target cells treated with Triton X-100 (target maximum LDH release).

After 20 h of incubation for cell lysis, 50 µl of supernatant from each well was carefully transferred to a new flat-bottom 96-well plate for LDH release measurement.

Reconstituted LDH substrate mix (50 µl/well) was added to each well of the enzymatic assay plate containing samples transferred from the cytotoxicity assay plate.

After a 30 min-incubation in the dark at room temperature, 50 µl/well of stop solution was added and absorbance was measured at 490 nm.

The percent specific lysis of each sample was determined using the formula:

percent specific lysis=(LDH release from sample value−effector spontaneous release−target spontaneous release)/(target maximum release−target spontaneous release)*100.

Figure 4:
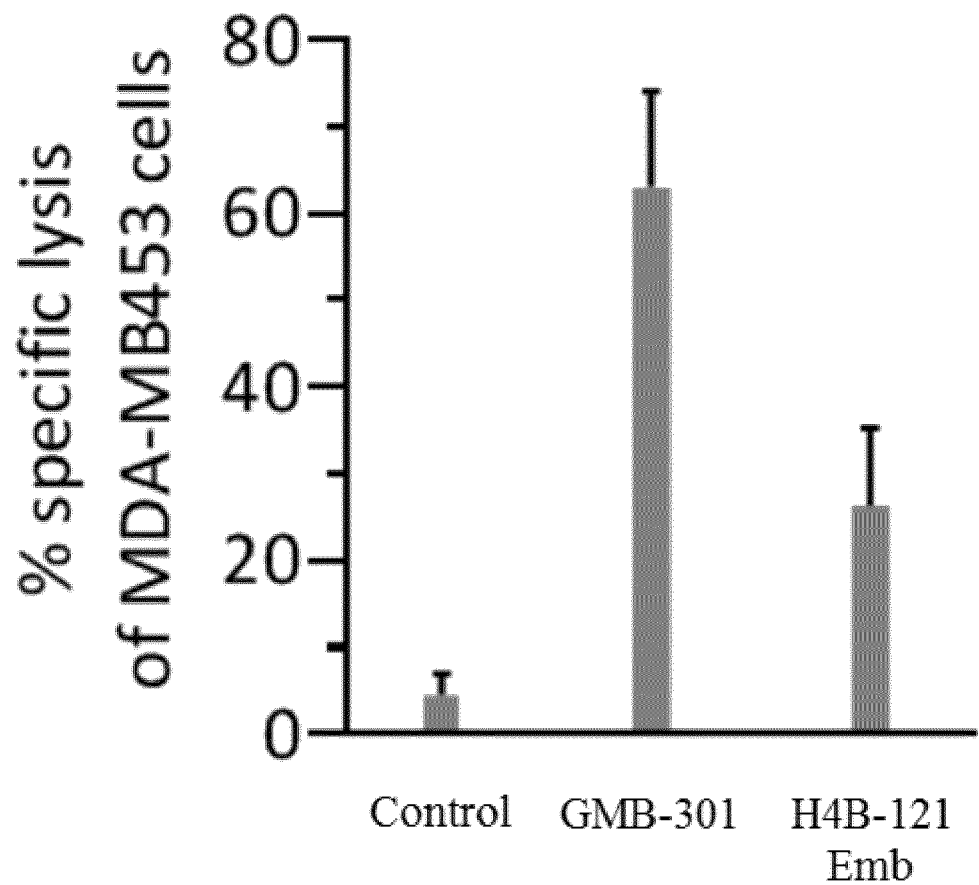
FIG. 4 shows the effects of a treatment with GMB301, the emabling version of the antibody H4B 121 or an antibody irrelevant (Controle Px) (1 µg/ml) on the cellular lysis (ADCC) of MDA-MB453 breast cancer cells in the presence of 100 ng/ml of NRG1 together with effector peripheral blood mononuclear cells (T:E ratio 1:15).

As shown in FIG. 4, GMB301 induces a stronger ADCC of MDA-MB-453 tumor cells (about 65% lysis) than the emabling version of the H4B-121 antibody (about 25% lysis).

Example 5: Low-Fucose Anti-HER3 Antibodies H4B-121-Emb and GMB301, Produced in YB2/0 Cells, Bind to the HER3 Receptor with Similar Affinity Recombinant human HER3 extracellular domain (ECD) was purchased from R&D Systems and the H4B-121 was produced as indicated in example 4.

Nunc Maxisorp plates were coated with 50 ng/well recombinant human HER3 ECD for 16 hours at 4° C. and were blocked with 2% BSA in PBS. Anti-HER3 antibodies GMB301 and H4B-121-emb were serially diluted from 0.5 µg/ml to 1 ng/ml (3 nM to 6.5 pM) and incubated 1 hour at 37° C.

After washes with PBS containing 0.1% Tween 20, bound anti-HER3 antibodies were detected by a conjugated HRP-F(ab')2 goat anti human $F(ab')_2$ specific antibody (Interchim).

After two hours at 37° C. and three washes, TMB (3,3,5,5 tetramethylbenzidine, Sigma) was used as substrate for detecting peroxidase activity, 1M H2SO4 was added to stop the reaction, plate was read at 450 nm and binding data curves were analysed using four-parameter nonlinear regression fit from GraphPad Prism.

As shown in FIG. 4, H4B-121-Emb and GMB301 bind to the HER3 receptor with similar affinity H4B-121-emb having an EC50 of 0.11 nM+/−0.02, while GMB301 has an EC50 of 0.19 nM+/−0.01.

Example 6: GMB301 is More Efficient to Reduce Tumor Growth and to Increase Survival Time of NRG1-Addicted Tumors than Antibody H4B-121 Emabling The H4B-121 was produced as indicated in example 4.

Athymic, 6- to 8-week-old, female BALB/c nude mice were purchased from Janvier and Charles Rivers Laboratories. NRG1-addicted pancreatic BxPC3 (3×106), triple-negative breast cancer HCC-1806 (1×106) and lung A549 cancer cells (4×106) were injected s.c. into the right flank of athymic BALB/c nude mice.

All in vivo experiments were done in compliance with the French guidelines for experimental animal studies (Agreement no. B34-172-27).

Tumor-bearing mice were randomized in the different treatment groups when the tumors reached an approximate volume of 120-150 mm3. The mice were treated by i.p. injections of GMB301 vs H4B-121-Emb vs vehicle (NaCl—negative control). The amount of injected antibody was 300 µg/injection (15 mg/kg), twice a week, for 4 weeks consecutively (Q3D-4W).

Tumor dimensions were measured one weekly with a caliper and the volumes were calculated by the formula D1×D2×D3/2.

As shown in FIG. 5, left panel, a greater reduction of NRG1-addicted BxPC3, HCC-1806 and A549 tumor growth is observed in GMB301-treated mice, with regard to mean tumor size measured in mice treated with control or with antibody H4B-121-emb.

In correlation, a greater benefit (gain in days of treatments vs control group) was observed in the group treated with GMB301 vs group treated with H4B-121-emb in the three models of xenografted NRG1-addicted tumors (BxPC3: +21 days for GMB301 vs+14 days for H4B-121-emb group; HCC-1806: +21 days for GMB301 vs+7 days for H4B-121-emb; A549: +21 days for GMB301 vs −7 for H4B-121-emb) (FIG. 5, right panel).

The invention claimed is:

1. A neuregulin non competitive allosteric anti-human HER3 antibody comprising:
   (a) a heavy chain wherein the variable domain comprises:
   a H-CDR1 having a sequence set forth as SEQ ID NO: 2;
   a H-CDR2 having a sequence set forth as SEQ ID NO: 3; and
   a H-CDR3 having a sequence set forth as SEQ ID NO: 4; and
   (b) a light chain wherein the variable domain comprises
   a L-CDR1 having a sequence set forth as SEQ ID NO:6,
   a L-CDR2 having the amino acid a sequence SAS; and
   a L-CDR3 having a sequence set forth as SEQ ID NO:8;
   said antibody having a human constant region; and
   less than 65% of the glycan structures carried by the glycosylation sites of the antibody comprise a fucose molecule.

2. The antibody of claim 1, comprising a light chain variable region comprising a L-CDR1 having a sequence set forth as SEQ ID NO:6, a L-CDR2 having the amino acid sequence SAS and a L-CDR3 having a sequence set forth as SEQ ID NO:8.

3. The antibody of claim 1, wherein the heavy chain variable region of said antibody has the amino acid sequence set forth as SEQ ID NO: 1 and/or the light chain variable region has the amino acid sequence set forth as SEQ ID NO: 5.

4. The antibody of claim 3, wherein the heavy chain variable region of said antibody has the amino acid sequence set forth as SEQ ID NO: 1 and the light chain variable region has the amino acid sequence set forth as SEQ ID NO: 5.

5. The antibody of claim 1, wherein the heavy chain of said antibody has the amino acid sequence set forth as SEQ ID NO: 9 and/or the light chain of said antibody has the amino acid sequence set forth as SEQ ID NO: 10.

6. The antibody of claim 5, wherein the heavy chain of said antibody has the amino acid sequence set forth as SEQ ID NO: 9 and the light chain of said antibody has the amino acid sequence set forth as SEQ ID NO: 10.

7. The antibody according to claim 1, wherein less than 50% of the glycan structures carried by the glycosylation site of the antibody comprise a fucose molecule.

8. The antibody of claim 1 which is a chimeric antibody.

9. The antibody of claim 8 which is a humanized antibody.

10. A nucleic acid sequence encoding an antibody according to claim 1.

11. A vector comprising a nucleic acid according to claim 10.

12. A host cell comprising a nucleic acid according to claim 10 or a vector comprising the nucleic acid.

13. A pharmaceutical composition comprising at least an antibody according to claim 1 and a pharmaceutically acceptable carrier.

14. An immunoconjugate comprising the antibody according to claim 1 linked to a therapeutic agent.

15. A pharmaceutical composition comprising at least the immunoconjugate according to claim 14 and a pharmaceutically acceptable carrier.

16. A method for treating a cancer associated with the expression of HER3 wherein neuregulin is present in a subject in need thereof comprising administering to the subject a therapeutically effective amount of an antibody according to claim 1 or an immunoconjugate comprising the antibody linked to a therapeutic agent.

17. A method of inhibiting growth of tumor cells associated with the expression of HER3 wherein neuregulin is present in a subject in need thereof, comprising administering to the subject a therapeutically effective amount of an antibody according to claim 1 or an immunoconjugate comprising the antibody linked to a therapeutic agent.

18. The method according to claim 16, wherein neuregulin is secreted by the cancer and/or by tissues and/or organs surrounding the cancer.

19. The method according to claim 18, wherein the cancer is neuregulin-dependent.

20. The method according to claim 16, wherein neuregulin is present due to its administration to the subject before, after, or at the same time as the antibody and/or the immunoconjugate.

21. The method according to claim 16, wherein the cancer associated with the expression of HER3 is selected from the group consisting of squamous cell cancer, small-cell lung cancer, non-small cell lung cancer, gastric cancer, pancreatic cancer, glial cell tumors, such as glioblastoma and neurofibromatosis, cervical cancer, ovarian cancer, liver cancer, bladder cancer, hepatoma, breast cancer, colon cancer, melanoma, colorectal cancer, endometrial carcinoma, salivary gland carcinoma, kidney cancer, renal cancer, prostate cancer, vulval cancer, thyroid cancer, hepatic carcinoma and head and neck cancers.

* * * * *

SEQUENCE LISTING

<160> NUMBER OF SEQ ID NOS: 10

<210> SEQ ID NO 1
<211> LENGTH: 117
<212> TYPE: PRT
<213> ORGANISM: Mus musculus

<400> SEQUENCE: 1

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Tyr Ile Ser Asp Gly Gly Val Thr Tyr Tyr Pro Asp Thr Ile
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Asp Arg Tyr Gly Leu Phe Ala Tyr Trp Gly Gln Gly Thr Leu
            100                 105                 110

Val Thr Val Ser Ala
        115

<210> SEQ ID NO 2
<211> LENGTH: 8
<212> TYPE: PRT
<213> ORGANISM: Mus musculus

<400> SEQUENCE: 2

Gly Phe Thr Phe Ser Ser Tyr Thr
1               5

<210> SEQ ID NO 3
<211> LENGTH: 8
<212> TYPE: PRT
<213> ORGANISM: Mus musculus

<400> SEQUENCE: 3

Ile Ser Asp Gly Gly Val Thr
1               5

<210> SEQ ID NO 4
<211> LENGTH: 10
<212> TYPE: PRT
<213> ORGANISM: Mus musculus

<400> SEQUENCE: 4

Ala Arg Asp Arg Tyr Gly Leu Phe Ala Tyr
1               5                   10

<210> SEQ ID NO 5
<211> LENGTH: 107
<212> TYPE: PRT
<213> ORGANISM: Mus musculus

<400> SEQUENCE: 5

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Ile Ala

```
                    20                  25                  30
Val Ala Trp Tyr Gln Gln Lys Pro Gly Gln Ser Pro Lys Leu Leu Ile
            35                  40                  45

Tyr Ser Ala Ser Asn Arg Tyr Thr Gly Val Pro Asp Arg Phe Thr Gly
        50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Ser Asn Tyr Pro Tyr
                85                  90                  95

Thr Phe Gly Gly Gly Thr Lys Leu Glu Ile Lys
            100                 105
```

<210> SEQ ID NO 6
<211> LENGTH: 6
<212> TYPE: PRT
<213> ORGANISM: Mus musculus

<400> SEQUENCE: 6

```
Gln Asn Val Gly Ile Ala
1               5
```

<210> SEQ ID NO 7

<400> SEQUENCE: 7

000

<210> SEQ ID NO 8
<211> LENGTH: 9
<212> TYPE: PRT
<213> ORGANISM: mus musculus

<400> SEQUENCE: 8

```
Gln Gln Tyr Ser Asn Tyr Pro Tyr Thr
1               5
```

<210> SEQ ID NO 9
<211> LENGTH: 447
<212> TYPE: PRT
<213> ORGANISM: Artificial Sequence
<220> FEATURE:
<223> OTHER INFORMATION: Synthetic polypeptide consisting of mus
      musculus SEQ ID NO: 1 followed by Cgamma chain isotype 1 of Homo
      Sapiens

<400> SEQUENCE: 9

```
Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Tyr Ile Ser Asp Gly Gly Val Thr Tyr Tyr Pro Asp Thr Ile
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Asp Arg Tyr Gly Leu Phe Ala Tyr Trp Gly Gln Gly Thr Leu
            100                 105                 110
```

```
Val Thr Val Ser Ala Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 10
<211> LENGTH: 214
<212> TYPE: PRT
<213> ORGANISM: Artificial Sequence
<220> FEATURE:
<223> OTHER INFORMATION: Synthetic polypeptide consisting of Mus
      musculus SEQ ID NO: 5 followed by Ckappa sequence of Homo sapiens

<400> SEQUENCE: 10

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Ile Ala
            20                  25                  30
```

```
Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Ser Asn Tyr Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```